RAPHIOLEPIS INDICA
Filed Sept. 9, 1968 2 Sheets-Sheet 1
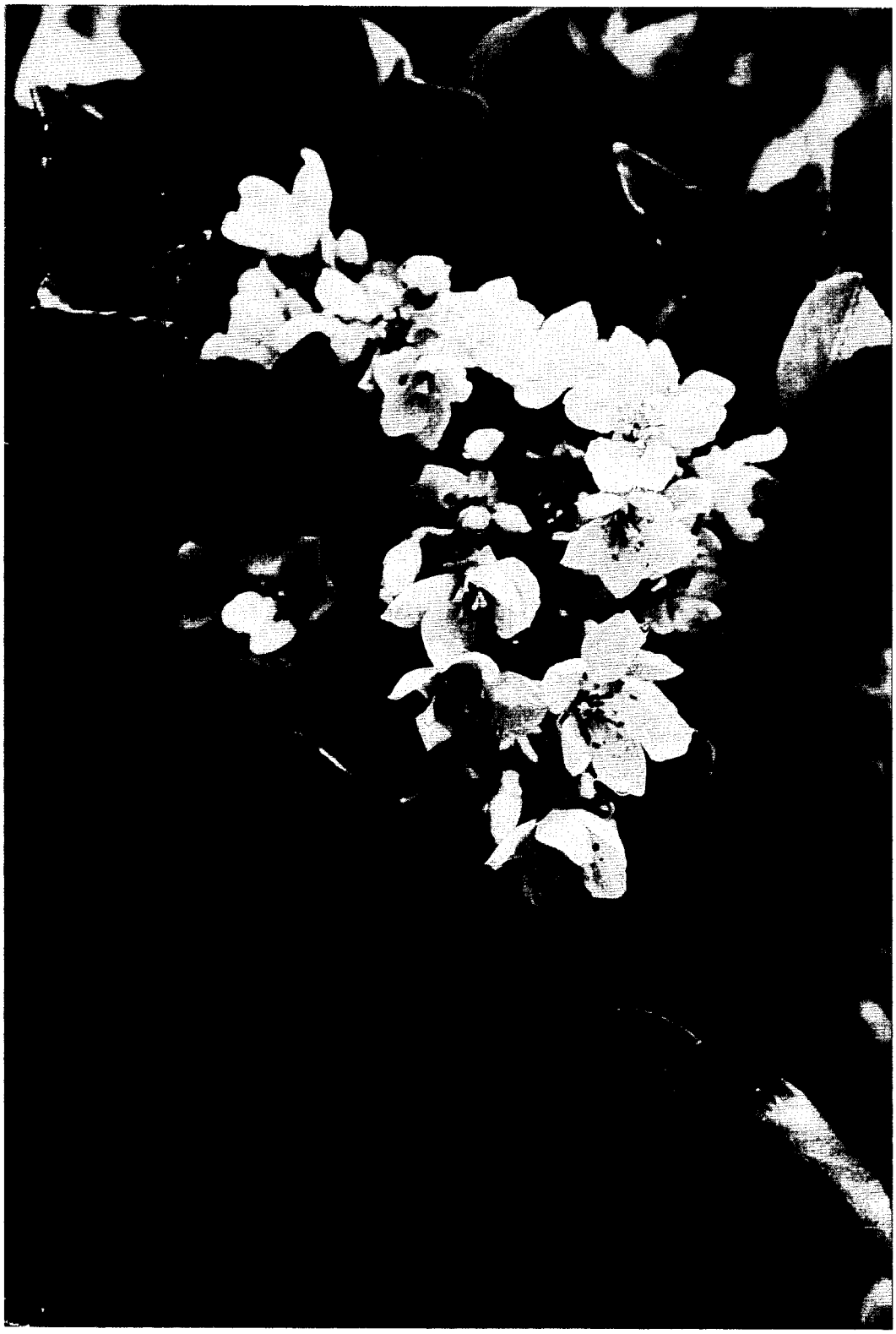

RAPHIOLEPIS INDICA
Filed Sept. 9, 1968 2 Sheets-Sheet 2
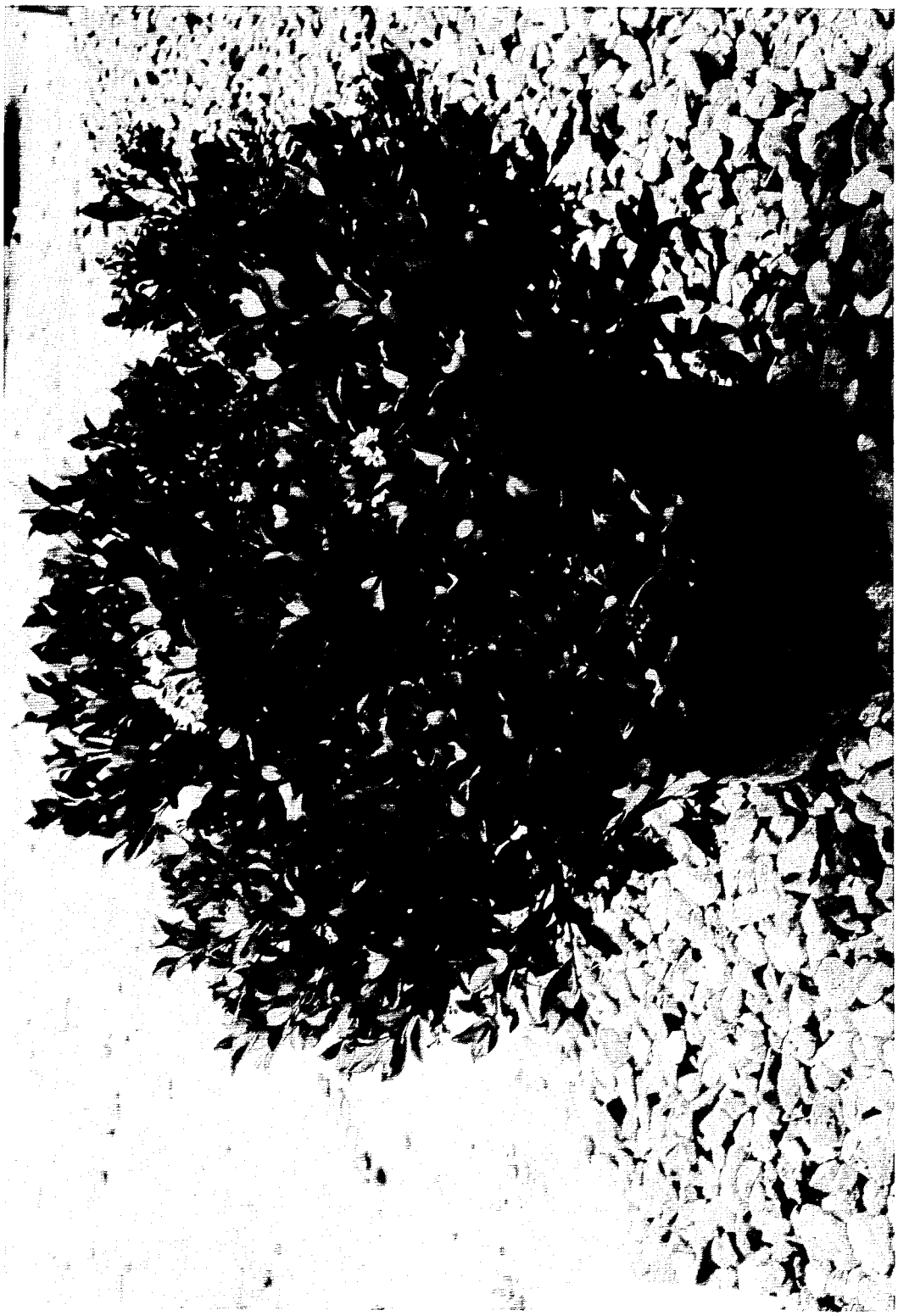

United States Patent Office

Plant Pat. 2,972
Patented June 23, 1970

2,972

*RAPHIOLEPIS INDICA*

Ernest P. Bordier, Glendora, Calif., assignor to Bordier's Nursery, Inc., Santa Ana, Calif.

Filed Sept. 9, 1968, Ser. No. 758,633
Int. Cl. A01h *5/00*
U.S. Cl. Plt.—54 1 Claim

The present invention relates to a new and distinct variety of *Raphiolepis indica* plant and more particularly to a plant of this genus (family Rosaceae) which is an evergreen shrub.

I discovered this new variety on my cultivated property located at 1303 S. Bonnie Cove Ave., in the city of Glendora, county of Los Angeles, State of California, in March of 1963. The new variety originated as a chance seedling of cultivated *Raphiolepis indica* "Jack Evans," an unpatented hybrid, the pollen parent being unknown.

The new variety has been asexually reproduced by me on my cultivated property in Glendora, Calif., and my cultivated property located at 7231 Irvine Blvd., county of Orange, State of California, by cuttings. Thousands of cuttings of the new and distinct variety have been made since 1963, and in all instances the descendants have exhibited the distinguishing characteristics of the new variety, thereby establishing that the strain is true. The plant cannot be reproduced true from seed.

My new and distinct variety is characterized as to novelty by its satiny green foliage throughout most of the year, which turns to a satiny bronze appearing foliage in the cooler months; by its compact habit of mounding growth; by the broadly pyramidal shape of the panicle of the flowers; by the abundance and outstanding Amaranth Rose color of its flowers; and by the unique undulating shape of the leaves.

The new variety differs from its seed parent, *Raphiolepis indica* "Jack Evans," in the smaller size of its leaves, its more compact mounding growth habit, and by the color of its flowers which are Amaranth Rose, whereas the flowers of the parent plant are light pink in color. The panicles of flowers of the new variety are described as broadly pyramidal in shape and larger than the flowers of the seed parent which are clustered with no resolved shape in its flower panicles. The color of the leaves of the new variety show a bronzy appearance in the cooler months, while the leaf color of the seed parent shows no marked change throughout the year.

A detailed description of the new and distinct variety of *Raphiolepis indica* follows, and the accompanying illustrations in full color show the entire plant and an enlarged view of one of the panicles of flowers. To facilitate identification of the important colors, the color terminology adopted by the British Horticultural Colour Charts has been followed. The color of the leaves and flowers in the accompanying illustrations are as close as can be reproduced by this method of illustration.

THE PLANT

Type: Evergreen bush.

Parentage: Chance seedling from *Raphiolepis indica* "Jack Evans," unpatented variety, pollen parent unknown.

Growth habit: The bush has a compact mounding habit.

Size: The bush reaches a height of approximately three feet and a width that is four feet or more.

Foliage:

*Quantity.*—Abundant.

*Shape.*—The leaves are obovate to oblanceolate. The tip of the leaf is acute with the base of the leaf being attenuate, and the upper half being undulate, which adds greatly to the attractiveness of the plant and forms an admirable background to the blossoms.

*Size.*—The full grown leaves vary in size between two and three inches in length and are an inch to an inch and a quarter in width.

*Arrangement.*—The leaves are alternate on the stems.

*Color.*—Upper side—Ivy Green, 1060/1, page 200; underside—Spinach Green, 960/3, page 187.

*Appearance.*—Satiny.

*Petiole.*—Average one-half inch in length.

*Margins.*—The upper edge of the new leaf growth shows a reddish-brown coloring which disappears at maturity.

*Veins.*—Veins are depressed on the upper side, and are darker than the background on the under side.

*Texture.*—Leaves are coriaceous in texture.

THE FLOWER

Blooming habit: The plant blooms continuously from February through May, and puts out the greatest number of blooms in April and May. Some blooms will appear in August through October in southern California.

Shape of influorescence: The flowers are similar to those of *Raphiolepis indica,* and are formed in a broad pyramidal panicle.

Number of petals: Five petals form a flower.

Shape of petals: Obovate.

Peduncle: The flowers are attached to short peduncles which are from one-quarter to three-eighths of an inch in length. The peduncle is slightly hairy.

Color: The flower petals are Amaranth Rose 530/1.

Fragrance: Yes.

Sepals: Five sepals, united and tinged with red at the tips.

Note: These descriptions are based upon mature development produced on good soil in Los Angeles and Orange Counties, Calif.

Having described my invention, I claim:

1. A new and distinct variety of *Raphiolepis indica,* substantially as shown and described, characterized particularly as to novelty by the distinctive and unique coloring of the flowers which are Amaranth Rose; by the broadly pyramidal shape of the panicles of flowers; by the unique undulating shape of the leaves; by the shiny, satiny appearance of its leaves; by the satiny bronze appearance of its leaves in the fall and winter months; and by its compact mounding growth habit.

No references cited.

ROBERT E. BAGWILL, Primary Examiner